United States Patent [19]

Cerwin

[11] Patent Number: 4,519,501
[45] Date of Patent: * May 28, 1985

[54] LIGATING CLIP AND CLIP APPLIER PACKAGE

[75] Inventor: Robert J. Cerwin, Pittstown, N.J.

[73] Assignee: Ethicon, Inc., Somerville, N.J.

[ * ] Notice: The portion of the term of this patent subsequent to Nov. 1, 2000 has been disclaimed.

[21] Appl. No.: 487,437

[22] Filed: Apr. 21, 1983

Related U.S. Application Data

[63] Continuation-in-part of Ser. No. 284,413, Jul. 20, 1981.

[51] Int. Cl.³ .............................................. B65D 85/24
[52] U.S. Cl. .................................. 206/339; 206/63.3; 206/204
[58] Field of Search ...................... 206/63.3, 204, 225, 206/338, 339, 341, 347, 562, 570, 575, 370

[56] References Cited

U.S. PATENT DOCUMENTS

| | | | |
|---|---|---|---|
| 3,809,223 | 5/1974 | Kendall | 206/204 |
| 4,005,776 | 2/1977 | Seeley | 206/470 |
| 4,036,360 | 7/1977 | Deffeyes | 206/204 |
| 4,061,785 | 12/1977 | Nishino et al. | 206/204 |
| 4,076,120 | 2/1978 | Carrol et al. | 206/339 |
| 4,153,160 | 5/1979 | Leigh | 206/570 |
| 4,251,482 | 2/1981 | Sanderson et al. | 206/204 |
| 4,361,229 | 11/1982 | Mericle | 206/339 |
| 4,382,507 | 5/1983 | Miller | 206/204 |
| 4,408,603 | 10/1983 | Blake et al. | 206/339 |
| 4,412,617 | 11/1983 | Cerwin | 206/339 |

Primary Examiner—George E. Lowrance
Assistant Examiner—David T. Fidei
Attorney, Agent, or Firm—Robert L. Minier

[57] ABSTRACT

A package for hydrolyzable ligating clips including means for holding a plurality of clips and means for removing moisture from around the clips with an outer wrap surrounding the holding means, clips, and moisture removing means.

3 Claims, 6 Drawing Figures

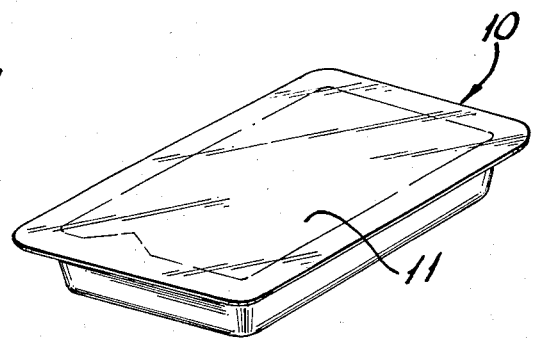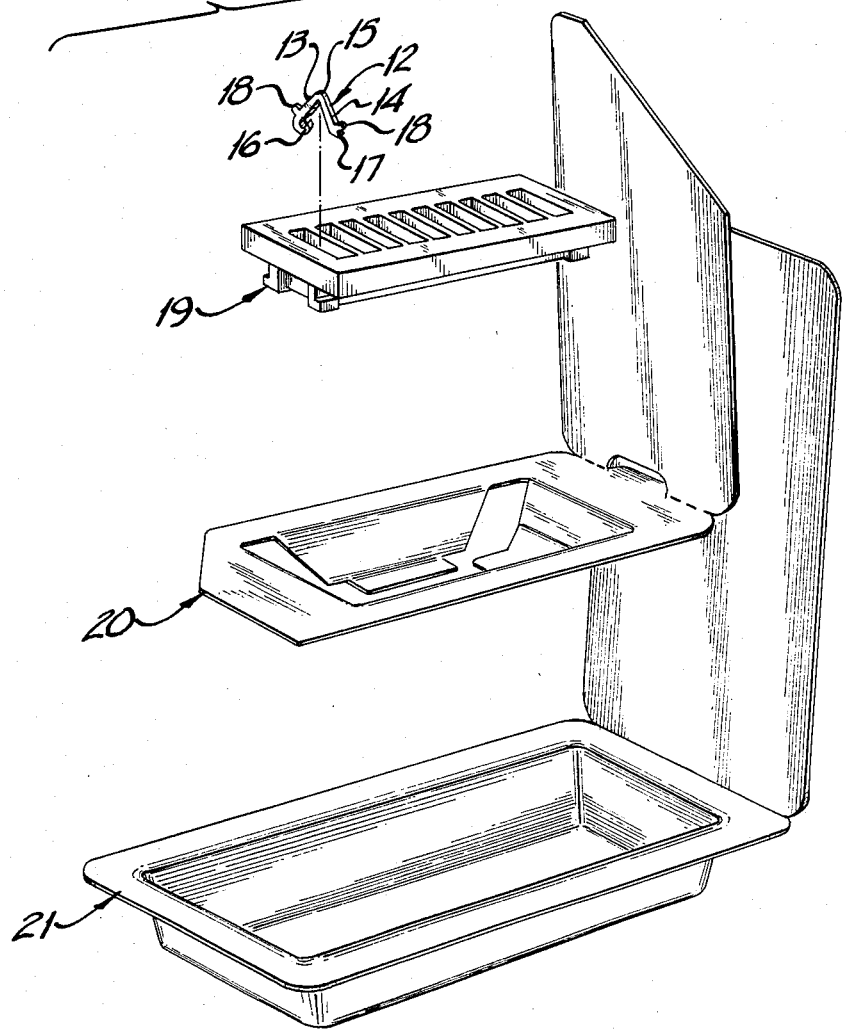

U.S. Patent   May 28, 1985   Sheet 2 of 3   4,519,501
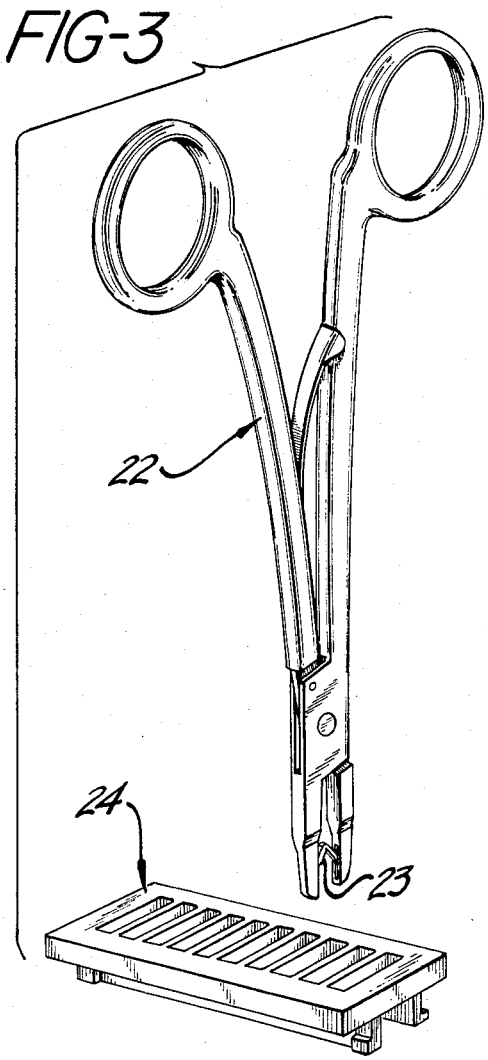
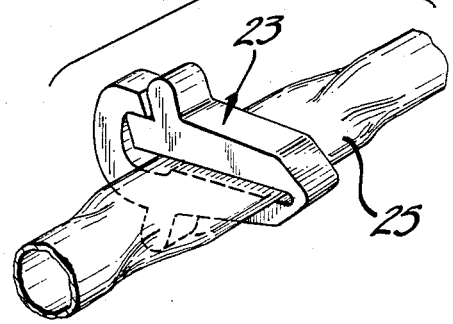
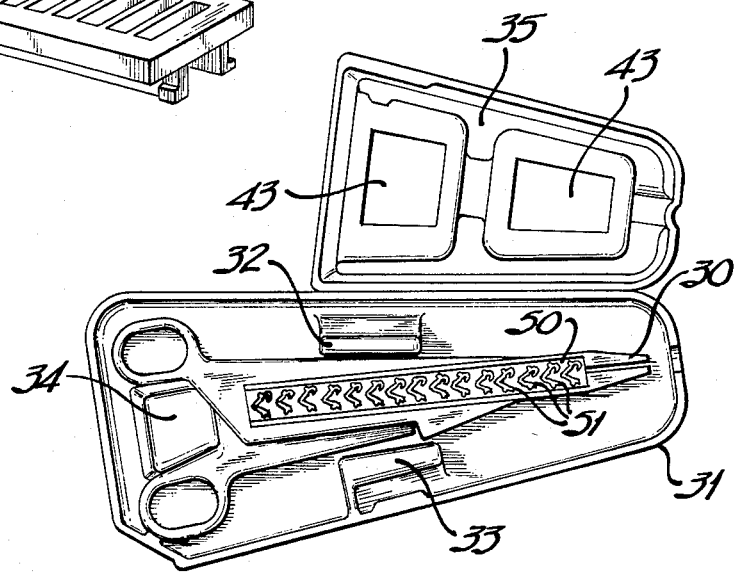

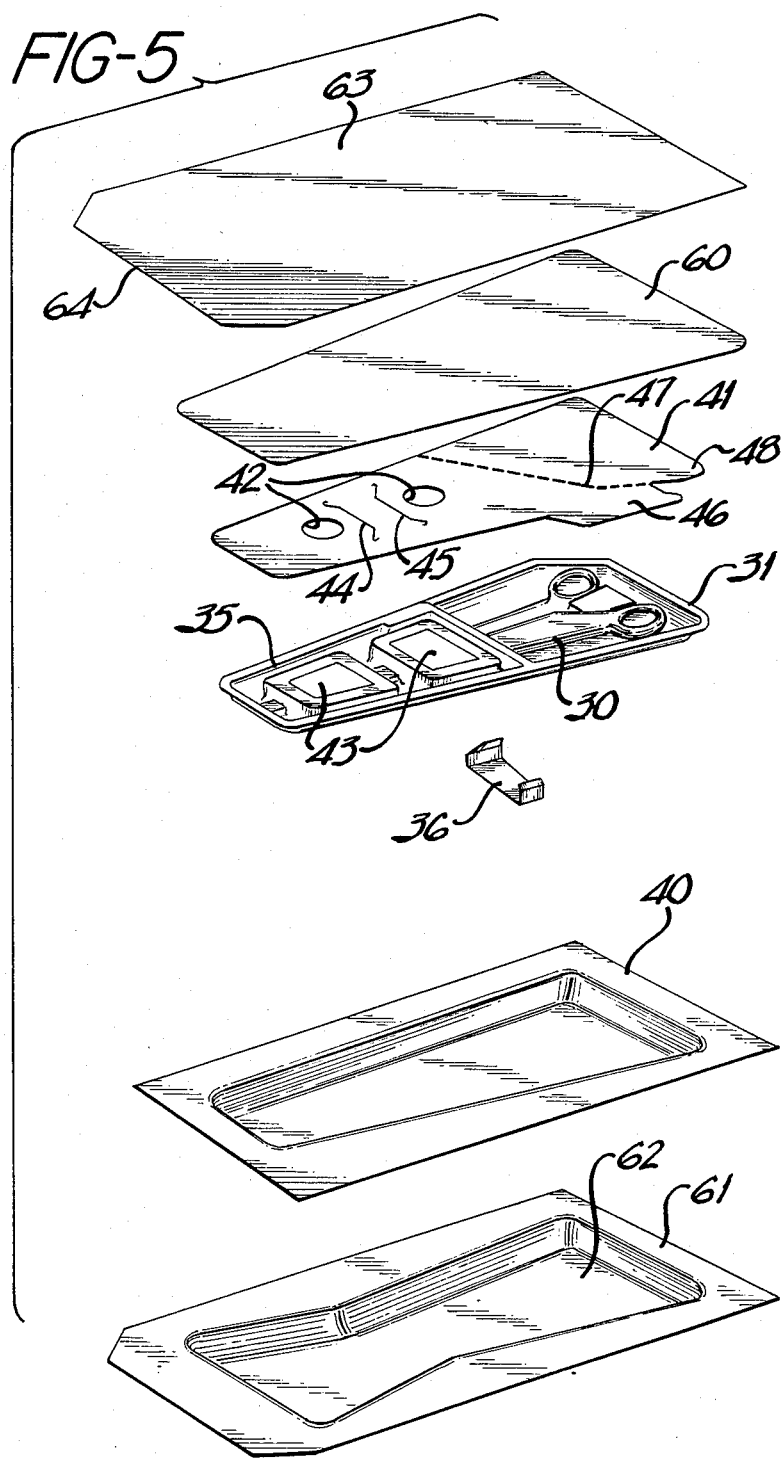

LIGATING CLIP AND CLIP APPLIER PACKAGE

RELATED APPLICATION

The present invention is a continuation-in-part application of copending application Ser. No. 284,413, filed July 20, 1981.

The present invention relates to a package for ligating clips and appliers and more particularly to packages for ligating clips made from absorbable polymers, which package has an extended shelf life.

BACKGROUND OF THE INVENTION

It is well known that in various medical procedures, synthetic devices, that is devices made from foreign materials, are very often implanted. Examples of such techniques are in surgery wherein various metals such as stainless steel, tantalum and other metal clips are used to control bleeding and are used to block off various blood vessels or other tubular organs during the surgical procedure. Also, in certain surgical procedures, various other metal rods, clips or sheets of materials are used for various supports or other reasons during the surgical procedure. In most instances, these devices remain in the patient for considerable periods of time, though in some instances they may be removed at some later date or even rejected by the natural physiological function of the human body. For the most part, these medical-surgical devices, even though they may cause no harm from the medical viewpoint, it is desired they not be allowed to remain in the body as they greatly disrupt post-operative X-ray procedures and subsequent diagnostic imaging of the patient. The metal materials not only disrupt the X-ray procedures, but they also disrupt other diagnostic procedures such as computerized axial tomography, and the like. Hence, it is desirous that the surgical devices be replaced by plastic materials that do not have a disruptive effect on the new diagnostic imaging procedure. It is even more desirable to make the medical devices, in many instances, out of absorbable polymers so that once they have completed the desired function, they are absorbed by the natural functioning of the human body and, hence, have no subsequent effect on diagnostic imaging or the like.

Sutures have for some time been made from absorbable polymers and have found considerable use in surgical procedures. It is well known that such suture materials should be packaged dry to prevent hydrolysis. Technique for producing such dry absorbable sutures are disclosed in U.S. Pat. Nos. 3,728,839 and 3,815,315. However, ligating clips have not been produced from absorbable polymers for a number of reasons, primarily because of the difficulty in molding such small devices and producing these small devices with the requisite physical properties required in these clips. Furthermore, when producing the clips from absorbable polymers, the clips being extremely small are produced with little orientation and their susceptability to be hydrolyzed is great. This requires that the clips be packaged in absolutely air-tight packages in order to have a sufficient shelf life to allow such clips to be sold and promoted for surgical procedures. Ligating clips made from absorbable polymers have thin hinge or bending areas which must be strong yet resilient and these areas are overly susceptible to hydrolysis. For such clips to have suitable shelf life, the hinge areas must be well protected against any moisture.

What I have discovered is an improved package which contains a plurality of ligating clips, the clips being made from absorbable polymer materials and having resilient hinges. Unexpectedly my new package maintains these clips in a condition for surgical use for extended shelf life periods even up to five years or more.

SUMMARY OF THE PRESENT INVENTION

The new package of the present invention contains a plurality of sterile, dry, hydrolyzable, surgical ligating clips. The package comprises a disposable means for holding the ligating clips in a spaced apart relationship. The clips are disposed in the holding means to provide an area around each clip for access thereto. The clips themselves have a pair of legs which are connected at their proximal ends by a narrowed resilient hinge portion. The hinge portion of the clip is more sensitive to hydrolysis than the remainder of the clip. The package also includes means for permanently removing moisture from the area around the clips and in the preferred embodiment of the present invention, the means for removing the moisture is pre-dried paper, though other means for removing moisture may also be used. The disposable holding means, the clips, and the moisture removing means are wrapped by an impermeable wrappers whereby the final package maintains the resiliency of the hinge portion of the clips over an extended shelf life period. Preferably, the clips of the present invention are made from polymers of dioxanone although they may be made from other of the absorbable polymer materials such as the homopolymers of glycolide, and lactide or copolymers of the same, or copolymers of either with dioxanone.

DESCRIPITON OF THE DRAWINGS

FIG. 1 is an enlarged perspective view of one type of package made in accordance with the present invention;

FIG. 2 is an exploded view in perspective of the package of FIG. 1 showing its component parts; and FIG. 3 is a perspective view depicting an instrument engaging a ligating clip in a disposable holder;

FIG. 4 depicts a clip in position closing off the lumen of a blood vessel;

FIG. 5 is an exploded view in perspective of another type of package of the present invention; and FIG. 6 is a plan view of a portion of the package depicted in FIG. 5.

DETAILED DESCRIPTION OF THE VARIOUS EMBODIMENTS

Referring to the drawings, in FIG. 1 there is shown a package 10 of the present invention. The outer wrapper 11 of the package in this instance is a foil material, with the foil being impermeable to maintain the item or device packaged sterile. In FIG. 2, is an exploded view of the package, in FIG. 1 showing its component parts. The package contains a plurality of ligating clips 12. The clips comprise a pair of leg members 13 and 14 connected at their proximal ends by a resilient hinge portion 15 and having disposed at the distal ends suitable locking means. In this instance, one end has a hook section 16 which, on closing the clip, engages the distal end 17 of the opposite leg member. However, it should be noted that other techniques for locking the distal ends of the clip are contemplated in accordance with the present invention. On the outer surface of each leg member, there is a boss 18. The bosses are used so that the clip can be engaged by a suitable instrument, removed from the holder, and placed in position to close off a blood vessel during the surgical operation. The clips are held in a disposable holding means 19. The means may be made out of plastic or other similar inexpensive materials. The clips are held in a manner so that the clips are spaced from each other and are readily available to be removed by a suitable instrument on an individual basis without interfering with adjacent clips. In this embodiment, the disposable holding means is wrapped in a kraft paper 20 and the kraft paper is used as a dessicant. The paper is a pre-dried paper which may be dried during the sterilization operation. The clips in the holder, plus the paper, are encased or wrapped in an impermeable outer wrapper 21. The outer wrapper may be foil or film or any of the various materials that would largely prevent bacteria, moisture or oxygen from permeating into the interior of the wrapper.

Referring to FIGS. 3 and 4, there is depicted the general technique for utilizing the ligating clips to close off a blood vessel during a surgical procedure. A suitable instrument 22, the end jaws of which are shaped to accept the bosses on the outer surfaces of the clip, remove a clip 23 from the disposable holding means 24. The clip disposed in the jaws of the instrument is placed about a blood vessel 25 and is closed by the instrument to close off the blood vessel as is more clearly shown in FIG. 4.

In certain embodiments of the present invention, the ligating clips are packaged along with an applier for applying a plurality of the clips. In certain instances the applier may be disposable and the clips packaged along with the applier and as an integral part of the applier. In other embodiments the clip may be packaged in a cartridge adapted to be used with a reusable multiple clip applier.

Referring to FIGS. 5-6 of the drawings, there is shown an embodiment of the package of the present invention. In this embodiment, an instrument 30 is held in a thermally formed polypropylene holding means 31. The instrument includes a cartridge 50 which holds a plurality of ligating clips 51 in spaced apart relationship. The clip may be sequentially fed to the gain of the instrument by appropriate mechanical means. The instrument is held by a holding means which is a support tray with an open top. The tray has formed areas 32, 33, and 34 which frictionally engage portions of the instrument to hold the instrument in place in a desired position. The thermally formed means includes a flap means 35 connected along a portion of one edge of the tray and which folds over on top of the instrument and partially closes the open side of the tray. Cooperating with the thermally formed tray is a rigid means 36 which sits in the reverse hollow areas of areas 32 and 33 of the thermally formed tray and cooperates with those areas to hold the instrument in the desired position in the tray even while the tray is being sterilized, shipped, handled, etc. The thermally formed polypropylene tray sits in a formed foil tray 40. The formed foil tray is made of a two mil aluminum foil which is Mylar* reinforced and which has a vinyl heat seal coating on one surface that comprises the outer periphery of the tray. Positioned on top of the thermally formed tray 31 is a paper insert member 41. The insert member is more clearly shown in FIG. 4. The paper member is dry and is an absorbing means. The paper member has a greater affinity for moisture than any portion of the clips in the cartridge. The paper member has sufficient absorbent capacity to maintain the clips dry and sterile for so long as they are in the unopened package. This paper insert member also serves to provide for easy or ready access to the instrument as will be more fully described hereinafter. The insert includes openings 42 superimposed over the openings in the flap 43 to provide for circulation of gases throughout the entire package during sterilization. The insert also includes two cut-out portions 44 and 45 which position the insert correctly with regard to the flap 15 and the thermally formed tray 11. The insert includes a die cut area 47 and a pair of tabs 46 and 48. The tabs are caught or inserted in the periphery of the outer wrapping so that when the outer wrapping is torn where indicated the tab 48 also tears and the paper insert is torn across the die cut area. A foil top member 60 made of material similar to the foil tray is positioned over the paper insert and is heat sealed to the periphery of the formed foil tray to totally encase the instrument, formed holding means, rigid holding means, and paper insert.

The package is overwrapped in a second thermo formed outer tray 61 in which the encased instrument package is positioned. The shape of the depression 62 in the outer tray is such as to readily allow a hand to grasp the inner package. This outer tray also may be made from polypropylene or other suitable material. The lid 63 for the tray is made of Tyvek* fabric, fabric sold by DuPont and which is a polyolefin spunbonded material. The Tyvek lid is sealed to the outer periphery of the thermoplastic tray by a peelable seal which may be readily opened from one end 64. The entire package is sterilized.

Hence, as described, ligating clips are one-piece clips and when made from plastic absorbable polymers are made with an area that acts as a hinge area to connect the two leg or vessel clamping portions of the clip. Using the absorbable polymers to make the ligating clips, the resilient hinge portion must be extremely narrowed or thinned to make it resilient and flexible. As is seen in FIG. 1, the clip has a hinge portion that is considerably narrower with regard to the remainder of the clip. This thin narrow area is very susceptible to hydrolysis and, hence, when making the clips from absorbable polymers, it is extremely important that the clips be protected from any water or any moisture whatsoever. The resilient hinge area or thinned area of the clip is much more sensitive to being attacked by moisture than the remainder of the clip. This problem makes it very difficult to produce a clip that has an extended shelf life. The sterile packages of the clips may require a shelf life of two, three, or even more years and, hence, because packages are not absolutely impermeable to all moisture for such extended periods, it is difficult to produce a package of absorable ligating clips that has such an extended shelf life. What I have discovered is that by placing in the package a suitable member that has a greater affinity for moisture than the very narrow portion of the clip and in fact will scavenge all moisture from the area surrounding the clip, I can extend the shelf life of the clip to that required to make absorbable clips readily available to the surgeons for various surgical procedures.

The following table shows the advantages of the new packages of the present invention. Ligating clips having the configuration as described in conjunction with FIG. 2 are subjected to an accelerated aging test. In this test the clips are packaged with a controlled amount of moisture present and then maintained at a temperature of 50° C. for a four-week period. The hinge strength of the clip is then determined. Some of the clips are implanted in rats. After seven days, a portion of the clips are harvested from the rats and the hinge strength of the clip determined. After fourteen days the remainder of the clips are harvested from the rats and the hinge strength of the clips determined. The result of these tests are given in the following table:

TABLE

| Amount Water Present (Micrograms) | Package | Hinge Strength (Lbs.) | | |
|---|---|---|---|---|
| | | 0 days | 7 days | 14 days |
| | | (after 4 wks. aging) | | |
| 700 | With Kraft Paper Wrapper | 6.73 | 3.47 | 1.23 |
| $10^4$ | With Kraft Paper Wrapper | 6.69 | 3.41 | 1.09 |
| $10^4$ | Without Kraft Paper Wrapper | 0 | 0 | 0 |

As may be seen from the previous table even with excess amounts of moisture present the clips packaged in accordance with the present invention maintain their in vivo properties. The clips not packaged in accordance with the present invention become very brittle and fragment either when they are removed from the cartridge or when attempting to close the clip.

The hinge strength of the clip is determined by conditioning the clips at 70° C. and 60% relative humidity for 16 hours. The distal ends of the clip are cut off and the cut ends of the clip placed in opposite steel faced jaws of an Instron Tensiometer. The jaws are displaced from each other at a stress rate of 5 mm/min. and the force required to break the clip hinge measured in pounds.

The clips of the present invention may be made from any of the well known absorbable polymers such as the homopolymers or copolymers of glycolide and lactide or the homo-polymers and copolymers of p-dioxanone,1-4,dioxipan-2-one and the various alkyl substituted derivatives thereof or any of the other well known absorbable polymers.

The package of the present invention may contain any suitable desiccant. Though pre-dried paper is preferred as the desiccant, it is possible to place other desiccants, such as silicia gel, or the like, within the package to produce the desired results. The package must, in its initial stage, be dry and the desiccant dried prior to the final packaging. This drying may be accomplished as part of the sterilizing operation. When sterilizing the absorbable clips with ethylene oxide the package may be totally dried after the sterilization step and the paper dried at that time so that after the package has been sterilized, the paper will act as the desired desiccant during the storage of the package.

Having now described the invention in detail, it should be readily apparent to one skilled in the art that there are various modifications and alterations which may be made without departing from the spirit and scope of the present invention.

We claim:

1. A package comprising:
   (a) a sterile instrument for applying a plurality of ligating clips;
   (b) means disposed within said instrument for holding a plurality of said ligating clips in spaced apart relationship to facilitate dispensing of the clips sequentially;
   (c) a plurality of sterile, dry, hydrolyzable surgical ligating clips disposed in spaced apart relationship in said holding means, each of said clips having a narrowed resilient hinge portion, said hinge portions being more sensitive to hydrolysis than the remainder of said clip;
   (d) absorbing means adjacent to said holding means said absorbing means having a greater affinity for moisture than any portion of said clip whereby any moisture present in said package, including moisture in the area around each clip, is preferentially absorbed by said absorbing means, said absorbing means having sufficient absorbent capacity to maintain the clips dry and sterile while in the unopened package;
   (e) and moisture impermeable outer wrap disposed in sealing relationship with respect to the instrument the holding means, clips, and moisture absorbing means, whereby said initially dry and sterile clips are maintained dry and sterile until the package is opened to maintain the resiliency of the hinge portion of the clips for an extended shelf life period.

2. The package according to claim 1 wherein the clips are made from a polymer of p-dioxanone.

3. The package according to claim 1 wherein the means for permanently removing moisture comprises pre-dried paper.

* * * * *